(12) United States Patent
Kobayashi et al.

(10) Patent No.: US 6,697,514 B1
(45) Date of Patent: Feb. 24, 2004

(54) APPARATUS FOR INSPECTING A FLUORESCENT SUBSTANCE ON A PLASMA DISPLAY

(75) Inventors: Akira Kobayashi, Osaka (JP); Masatoshi Nakamura, Takarazuka (JP); Ryoichi Inoue, Izumi (JP); Tsuyoshi Nomura, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 622 days.

(21) Appl. No.: 09/629,365

(22) Filed: Aug. 1, 2000

(51) Int. Cl.7 .................................................. G06K 9/00
(52) U.S. Cl. .................... 382/141; 382/260; 315/169.4; 313/489
(58) Field of Search ................................. 382/141, 148, 382/149, 166, 162, 274, 282, 260; 348/92, 128, 180, 173, 739, 790; 315/169.4; 313/485, 489, 484, 487, 467, 474; 345/60, 63, 65, 76, 41, 66, 72

(56) References Cited

U.S. PATENT DOCUMENTS

| | | | | |
|---|---|---|---|---|
| 4,758,728 A | * | 7/1988 | Matey et al. | 250/459.1 |
| 5,393,255 A | * | 2/1995 | Hisaoka et al. | 445/63 |
| 5,663,569 A | * | 9/1997 | Hayano | 250/559.45 |
| 5,717,780 A | * | 2/1998 | Mitsumune et al. | 382/141 |
| 5,790,913 A | * | 8/1998 | Roberts, Jr. et al. | 396/546 |
| 5,876,884 A | * | 3/1999 | Maeda et al. | 430/22 |
| 5,928,821 A | * | 7/1999 | Garrity, Jr. et al. | 430/23 |
| 6,184,849 B1 | * | 2/2001 | Stoller | 345/72 |

* cited by examiner

Primary Examiner—Jayanti K. Patel
Assistant Examiner—Sheela Chawan
(74) Attorney, Agent, or Firm—Jordan and Hamburg LLP

(57) ABSTRACT

An apparatus for inspecting the coating of a fluorescent substance on a plasma display panel includes an illumination device for irradiating UV light onto the fluorescent substance for causing the fluorescent substance to emit light, and an imaging device for picking up the emission of the fluorescent substance. A filter, that lets only light of certain wavelengths in accordance with light emission characteristics of the fluorescent substance pass, is arranged between the imaging device and the panel being inspected.

21 Claims, 7 Drawing Sheets

APPARATUS FOR INSPECTING A FLUORESCENT SUBSTANCE ON A PLASMA DISPLAY

BACKGROUND OF THE INVENTION

The present invention relates to an apparatus for inspecting a fluorescent substance coated on a plasma display panel or a cathode-ray tube by image processing, that is used in a fluorescent substance coating step for the manufacture of plasma display panels or cathode-ray tubes.

Expectations are mounting that plasma displays can serve as large-scale high-precision displays for the coming multimedia age. Thus, suitable quality control at each step of the manufacturing process is becoming increasingly important, in addition to the efforts at reduction of the product costs. Most importantly, color mixing of red (R), green (G) and blue (B) must be quantitatively inspected after the fluorescent substances for light emission of each color have been coated on a panel. Accordingly, a speedy, highly reliable inspection method that can be performed in an in-line system is desirable with regard to mass-production of the plasma display.

A conventional inspection method of fluorescent substances on a plasma display panel is described below with reference to FIGS. 7 and 8.

In FIG. 7, a panel 32 that has been coated with fluorescent substances to be inspected is placed on a positioning table 31. An UV light illumination device 34 is provided for causing a fluorescent substance coating portion 33 on the panel 32 to emit light. A color TV camera 36 and a lens 37 are mounted as a set to a movable TV camera support portion 35. The color TV camera 36 is controlled by a color TV camera controller 38.

The image signals input from the color TV camera 36 are converted into numerical data representing, for example, 256 density levels in accordance with the density of the RGB image through an analog-digital converter 39, and input into an image processing unit 55 including a CPU, a ROM, a RAM and an I/O device.

The image processing unit 55 comprises an evaluation control unit (CPU) 40 to which commands are given from a main controller or a control panel, a processing area setting unit 41 for specifying the area to be processed, a color extraction unit 42 for extracting a certain color space in the processing area, a thresholding unit 43 for performing threshold processing based on the intensity in the extracted color space and for extracting a specific region of the image, an evaluation unit 44 for judging whether the fluorescent substance has been coated over a predetermined area, and a display/command unit 45 for displaying the detected results as, for example, acceptable or unacceptable, or displaying the results as images on a display of a computer terminal, and displaying the positions where a deficiency exists. The operation of an apparatus for inspecting the fluorescent substances on a plasma display panel with the above configuration is described below with reference to FIG. 8.

First, a panel 32 to be inspected is placed on the positioning table 31, and UV light is irradiated from the UV illumination device 34 to cause the fluorescent substance 33 to emit light. The light emitted by the fluorescent substance passes the lens 37 and is picked up by the color TV camera 36. The resulting image is converted into numerical data by the A/D converter 39, and input into the image processing unit 55 (step 1). Next, an area to be processed in the input image data is designated as the processing area (step 2), and a specific color is extracted from the image data in this processing area, wherein thresholding is performed (step 3). At step 4, characteristic features of the specified color area are extracted by measuring the area or other properties. Based on a comparison of these characteristic features with a registered reference value, the acceptability of the specified area is judged (step 5). If any defect is detected, such is displayed individually on the display of a computer terminal or the like, wherein the type of the deficiencies is indicated together with the detected location of these deficiencies (step 6).

However, because this inspection apparatus uses a regular color TV camera, the wavelength of the light emitted by the fluorescent substance cannot be converted precisely into RGB data, and it is difficult to identify delicate color mixing with high reliability. Furthermore, fast inspections that are suitable for in-line examination are difficult to realize.

SUMMARY OF THE INVENTION

It is therefore an object of the present invention to solve these and other problems of the related art and to provide an apparatus for inspecting the coating of a fluorescent substance on a plasma display panel, in which an examination of color mixing among PDP fluorescent substances is performed reliably and fast.

In order to attain these objects, an apparatus for inspecting the coating of a fluorescent substance on a plasma display panel in accordance with the present invention comprises:

a table on which a panel to be inspected, coated with a fluorescent substance is placed;

an illumination device for irradiating UV light onto the fluorescent substance for causing the fluorescent substance to emit light;

an imaging device for picking up an image of light emission of the fluorescent substance; and a filter provided between the imaging device and the panel, that lets only light of specified wavelengths in accordance with light emission characteristics of the fluorescent substance pass toward the imaging device.

According to the present invention, a filter is provided that lets only light of certain wavelengths depending on light emission characteristics of the fluorescent substance pass toward the pick-up unit, so that a highly sensitive optical system adjusted to the light emission characteristics of the fluorescent substance can be realized, and even delicate color mixing can be detected with high reliability.

The apparatus is further provided with a visible rays cutting filter that prevents direct irradiation of visible light from the illumination device into the imaging device, so that, visible light, which tends to cause difficulties when inspecting the emission colors of the fluorescent substances, can be reduced.

The illumination device comprises a mirror for focusing the UV light emitted radially from a light source at a position at a certain distance, so that the fluorescent substances of the PDP are caused to emit strongly by illumination from a constant distance.

The apparatus is further provided with a mechanism for decreasing oxygen concentration of an atmosphere at the location where UV light is irradiated by the illumination device onto the fluorescent substance below the oxygen density in air, so that attenuation of UV light is prevented, that is brought about by the absorption of UV light due to the oxygen.

The imaging device comprises photodetectors arranged in a line, and the coating of the fluorescent substance is inspected continuously by moving the imaging device relatively to a direction that is perpendicular to a direction in which the photodetectors are arranged. The apparatus further comprises a unit for individually thresholding signals that are input from the photodetectors, and a unit for checking for deficiency candidates based on run lengths, which are detected by the unit for thresholding.

While novel features of the invention are set forth in the preceding, the invention, both as to organization and content, can be further understood and appreciated, along with other objects and features thereof, from the following detailed description and examples when taken in conjunction with the attached drawings.

DESCRIPTION OF THE INVENTION

One embodiment of the present invention will be hereinafter described with reference to FIGS. 1 to 6.

Figure 1:
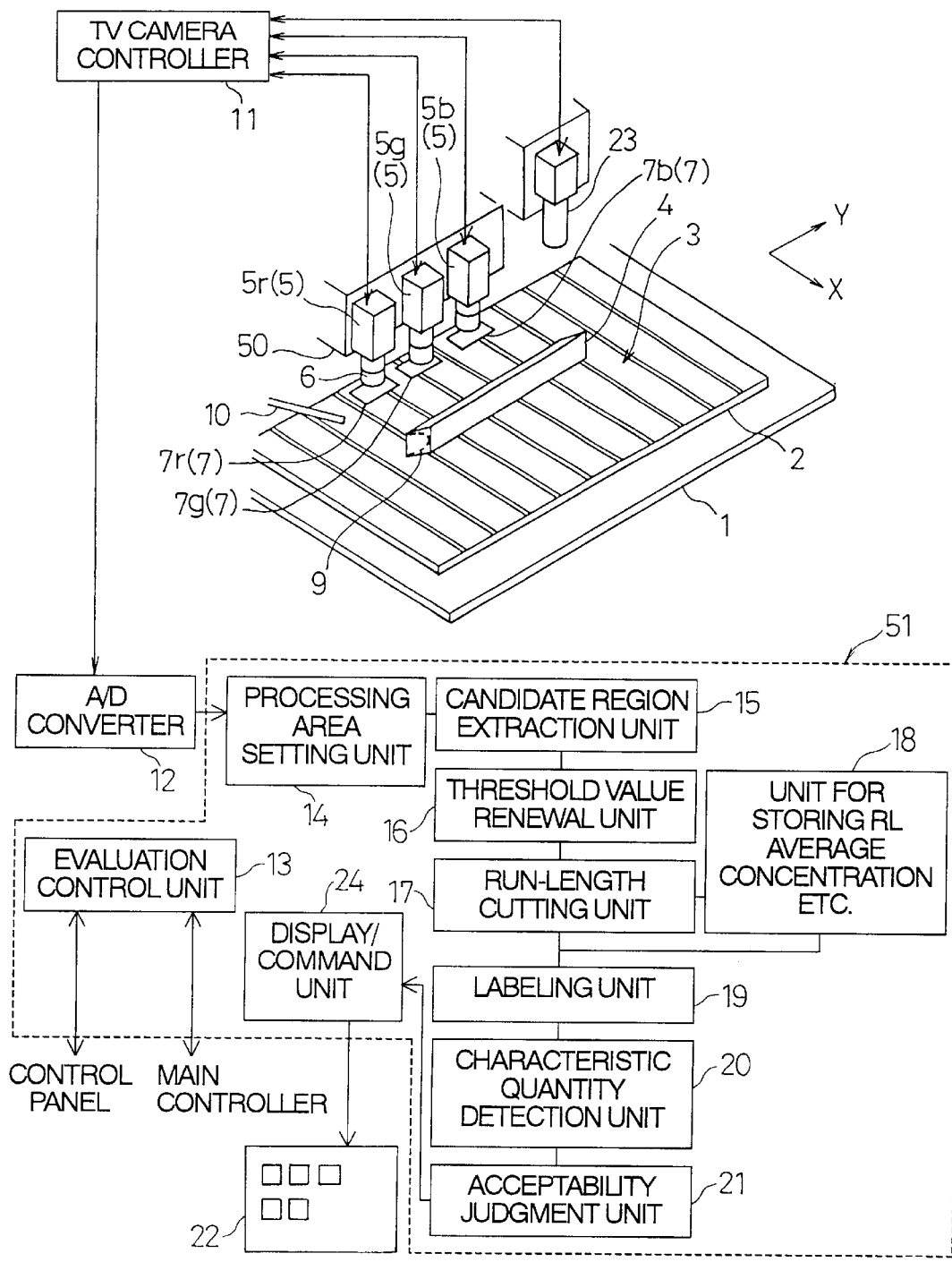
FIG. 1 is a diagram of an apparatus for inspecting a fluorescent substance on a plasma display in an embodiment of the present invention.
Figure 2:
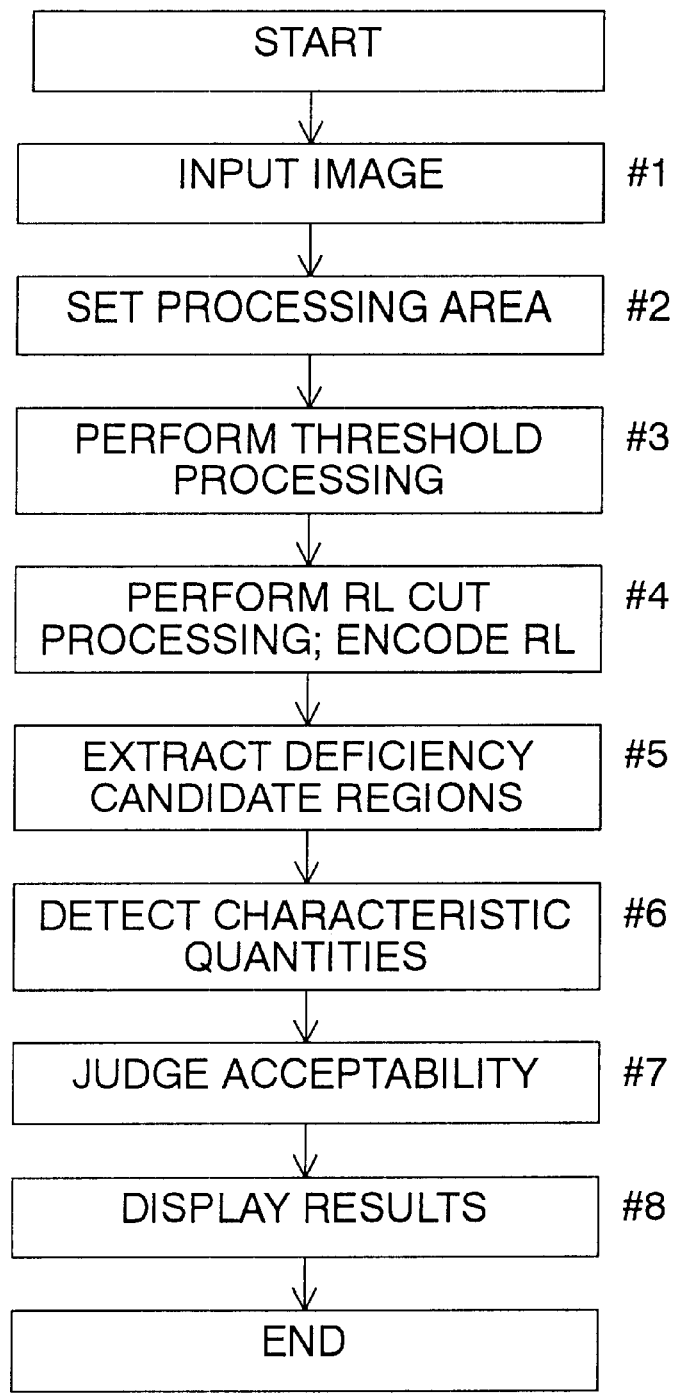
FIG. 2 is a flowchart illustrating the operation of the apparatus in FIG. 1.

FIG. 1 is a diagram showing an apparatus for inspecting the coating of a fluorescent substance on a plasma display in accordance with the present invention. FIG. 2 is a flowchart illustrating the examination procedure of this inspecting apparatus.

Figure 3:
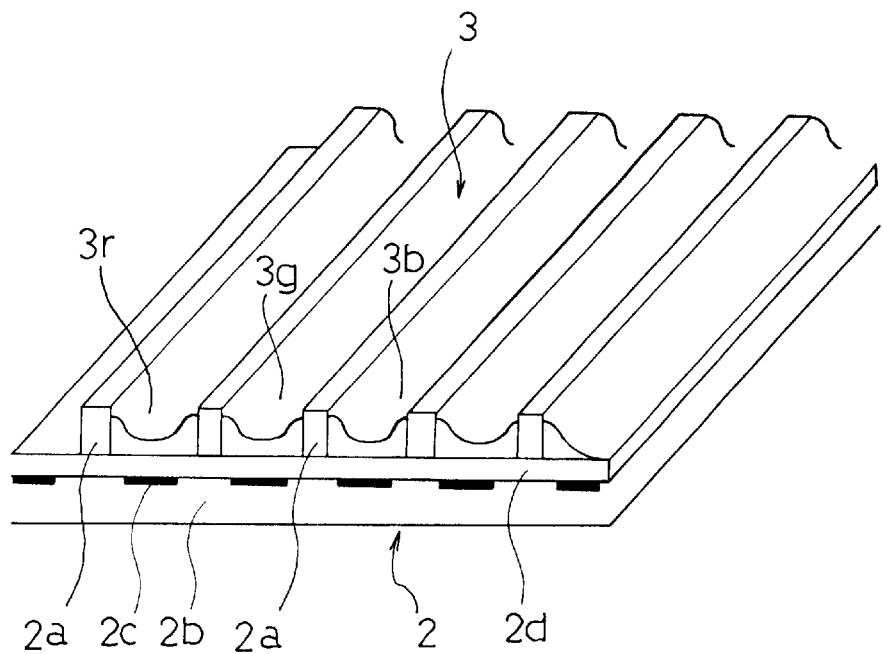
FIG. 3 illustrates the rear side of a PDP.

First, the fluorescent substance coating portion of the plasma display panel (PDP) 2 will be explained. FIG. 3 is a diagram showing the reverse side of the PDP 2. The PDP 2 shown in FIG. 3 includes ribs 2a, a glass substrate 2b, data electrodes 2c, and a dielectric layer 2d. However, there are also PDPS without a dielectric layer 2d. Usually, after the ribs 2a have been set up, fluorescent substances 3r, 3g and 3b for the colors R (red), G (green) and B (blue) are coated between the ribs 2a. The examination of the fluorescent substance 3 (as 3r, 3g and 3b are referred to generically) includes inspecting whether there are gaps or irregularities of the red, green and blue fluorescent substances 3 between certain ribs 2a, and whether they have been coated without mixing of the colors. When these fluorescent substances 3 are irradiated with light of a wavelength of UV rays, they emit light of a certain color or wavelength. The optical system of this examination apparatus includes an illumination device for irradiating light that includes UV light matching the light emission excitation characteristics of the red, green and blue fluorescent substances 3, for example of 220 nm to 240 nm wavelength, a line-shaped sensor that picks up the light that is emitted due to the illumination, and three band-pass filters for filtering light of certain specified wavelengths for red, green and blue respectively before the light enters the sensor. The examination is then performed by image processing these input signals.

The inspection apparatus in accordance with this embodiment is constructed as described below.

The object (PDP) 2 to be inspected is placed on a positioning table 1, and an illumination device 4 is arranged so as to irradiate, with light that includes UV rays, portions of the object (PDP) 2 that are coated with the fluorescent substances 3. It is also possible to use a device that filters the desired wavelengths from laser light as the illumination device 4.

To pick up the light that has been emitted by the illumination device 4, three TV cameras 5r, 5g and 5b equipped with line sensors such as CCDs or photomultipliers are mounted, together with lenses 6, on a movable TV camera support portion 50. When the light emitted from the fluorescent substances 3 is picked up by the TV cameras 5 (referring generically to the TV cameras 5r, 5g and 5b), three band-pass filters 7r, 7g and 7b (also collectively denoted by the numeral 7 in the following) for filtering light of certain specified wavelengths for red, green and blue, respectively, are placed in front of the TV cameras 5. For example, the band-pass filter 7r for red lets only light of 580 to 660 nm wavelength pass, the band-pass filter 7g for green lets only light of 500 to 580 nm wavelength pass, and the band-pass filter 7b for blue lets only light of 400 to 500 nm wavelength pass.

Figure 4:
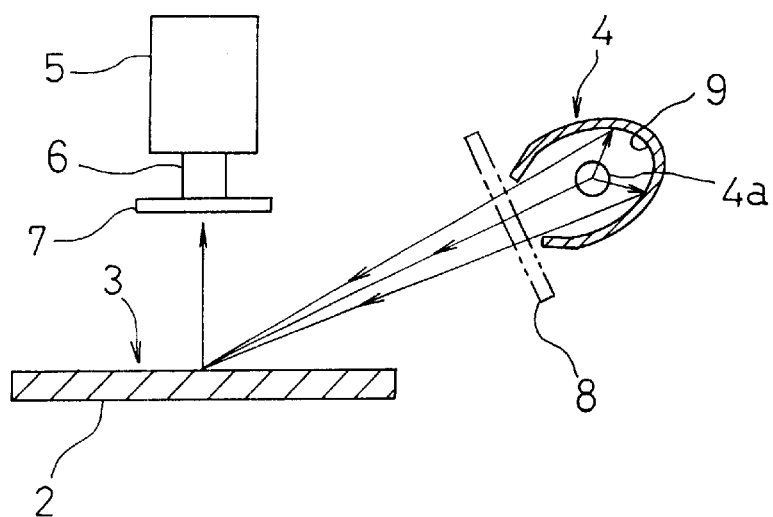
FIG. 4 illustrates an illumination device in an apparatus according to the present invention.

FIG. 4 shows the illumination device 4 in more detail. As shown, it is preferable to install a visible rays cutting filter 8, so that no visible light of the irradiation light is irradiated directly into the TV camera 5. The illumination device 4 is equipped with a lamp 4a, such as a fluorescent lamp, serving as the light source, and a reflection mirror 9, which focuses the illumination light at a predetermined distance from the lamp 4a in accordance with the distance between the lamp 4a and the object surface so as to increase the illumination/irradiation strength.

The apparatus further has a nitrogen dispensing nozzle 10 as shown in FIG. 1 for dispensing nitrogen gas or other inert gas, so as to create a low-oxygen atmosphere in which the density of oxygen is lower than that in air, in order to prevent the attenuation of the UV light for the emission of fluorescent light. The TV cameras 5 are controlled by a TV camera controller 11. The image signals input from the TV cameras 5 are converted into numerical data representing 0 to 255 density levels of the image through an analog-digital (A/D) converter 12, and input into an image processing unit 51 including a CPU, a ROM, a RAM and an I/O device.

The image processing unit 51 includes an evaluation control unit (CPU) 13 to which commands are given from a main controller or a control panel, a processing area setting unit 14 for specifying the area to be processed, a deficiency candidate extraction unit 15 for setting a threshold value and extracting a deficiency candidate region which is suspected of containing a defect, a unit 16 for renewing the threshold value, a run-length cutting unit 17 for discriminating deficiency candidate regions from noise based on the length of the regions (run-length) in one line that has been extracted by threshold value processing, a unit 18 for storing the run-length data of the remaining deficiency candidate regions and the average density data of the runs (storing the integrated density also results in storing the average density), a labeling unit 19 for performing a known labeling process with eight neighbor pixels, wherein different labels are assigned to each of the components where a series of pixels having a same value are connected, a characteristic quantity detection unit for detecting a plurality of characteristic quantities that represent features such as the surface area, from the individual deficiency candidate regions, an acceptability judgment unit 21 for judging the acceptability of the suspected regions based on the results of a comparison of the characteristic quantities with a registered reference value, and a deficiency display/command unit 24 for displaying the detected deficiencies on a display 22, for example of a computer terminal.

Numeral 23 denotes a review camera with high magnifying power for observing, or, for automatically reviewing the deficiencies that have been detected with the image processing unit 51. Although not shown, the apparatus may further comprise a command unit for displaying the images taken by the review camera 23 on the display 22.

Next, the operation of this plasma display inspection apparatus is described below.

In order to continuously inspect the portions of the PDP 2 placed on the positioning table 1 that have been coated with the fluorescent substances 3, the TV cameras 5r, 5g and 5b are moved in a direction X in FIG. 1. Irradiation with UV light from the illumination device 4 causes the R, G and B fluorescent substances 3 of the PDP 2 to emit light. The red, green and blue rays pass the band-pass filters 7 and the lenses 6, and are picked up by the TV cameras 5. The resulting images are converted with the A/D converter 12 into numerical data, and input into the image processing unit 51 (step 1 in FIG. 2).

Figure 5:
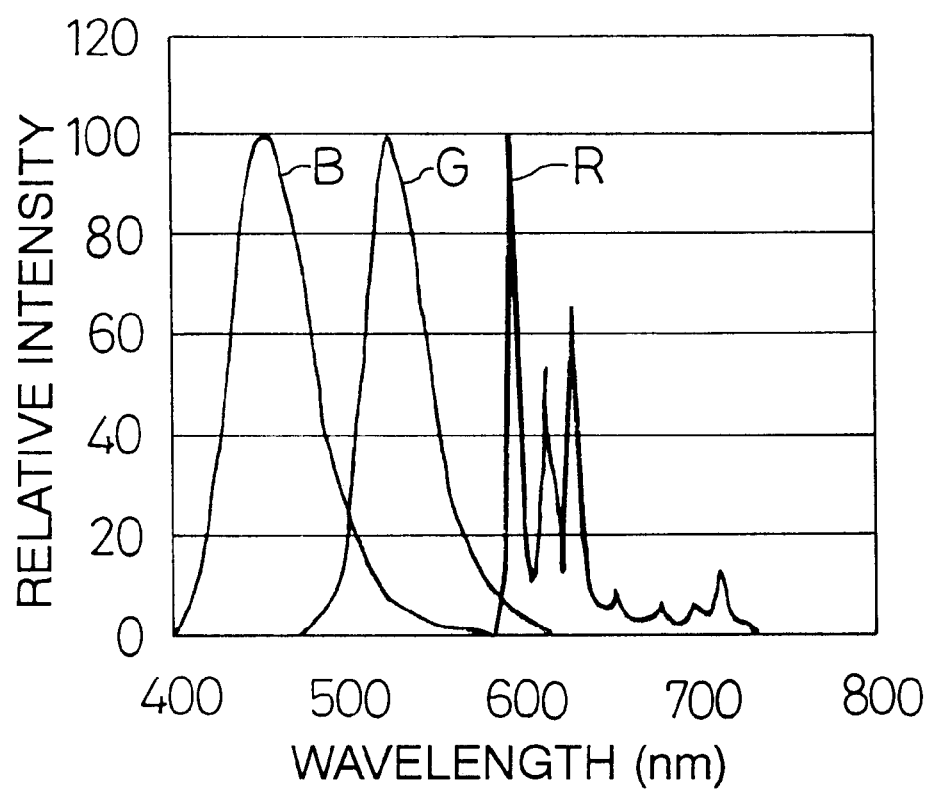
FIG. 5 illustrates the light emission excitation characteristics of fluorescent substances.

FIG. 5 shows the graphs of the light emission characteristics of the R, G, and B fluorescent substances. As can be seen, there are regions in which the emission wavelengths of each of the fluorescent substances overlap. If light with wavelengths of these intersecting regions is picked up by the RGB sensors, delicate color mixing cannot be identified. Accordingly, it is preferable to obtain light of the desired wavelengths by using the band-pass filters 7 that exclude the wavelengths of the overlapping regions and pass only light in wavelength bands that can be effectively used for the inspection. For example, from the signal that has passed the red band-pass filter 7r, deficiencies in which red fluorescent substance 3r has been coated into non-red fluorescent substance coating portions, gaps of the fluorescent substance in the red fluorescent substance region, or the adherence of contaminants in the red fluorescent substance region can be inspected. The image processing is performed in the manner described below.

Figure 6A:
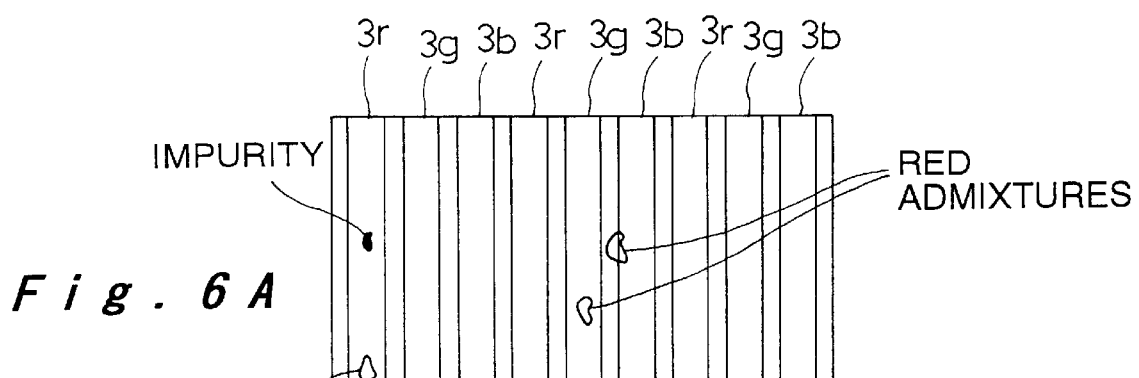
FIG. 6A illustrates different deficiencies of fluorescent substances.

FIG. 6A illustrates, firstly, the deficiency that red (R) fluorescent substance 3r is coated onto a rib 2a and into the coating portions of green (G) and blue (B) fluorescent substance 3g and 3b (color mixing of red fluorescent substance), secondly, a gap in the coating portion of red fluorescent substance 3r, and thirdly, the presence of contaminants.

Figure 6B:
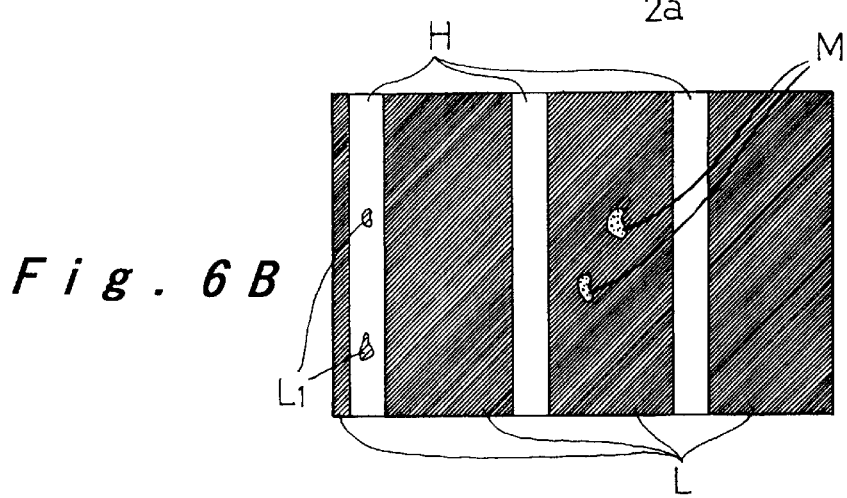
FIG. 6B illustrates the corresponding input image.
Figure 6C:
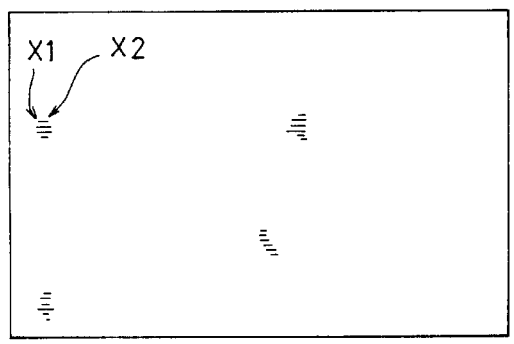
FIG. 6C illustrates the corresponding compression data of deficiency candidate regions.
Figure 7:
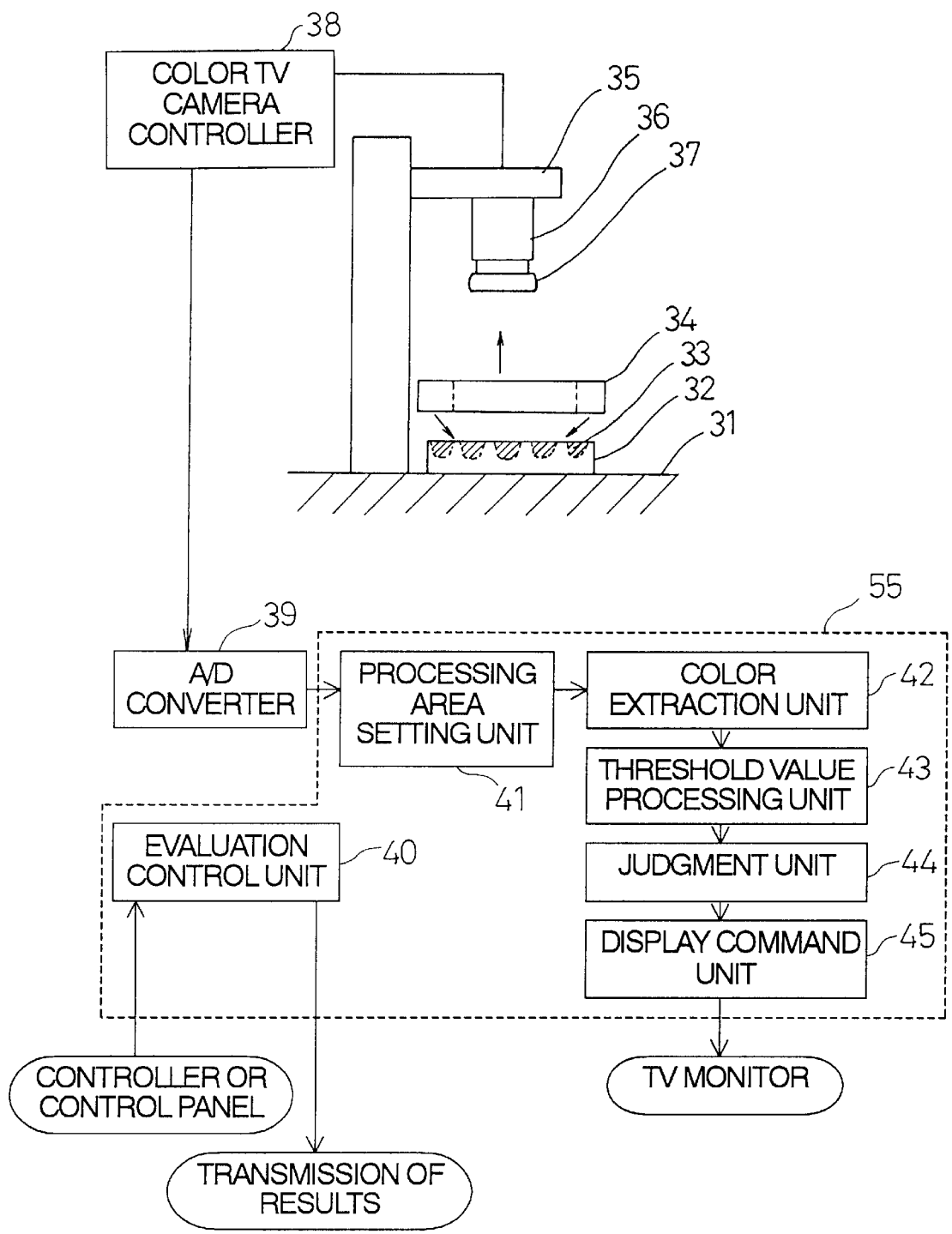
FIG. 7 is a diagram showing a conventional apparatus for inspecting a fluorescent substance on a plasma display.
Figure 8:
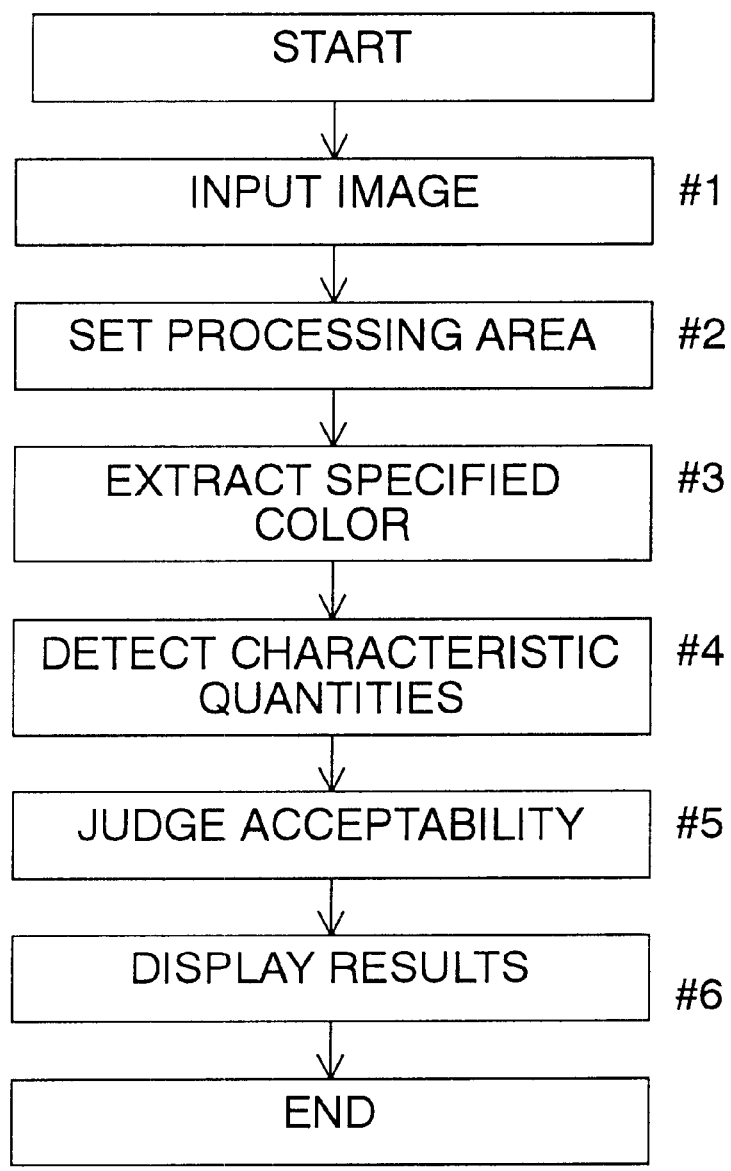
FIG. 8 is a flowchart illustrating the operation of the conventional apparatus in FIG. 7.

The TV cameras 5r, 5g and 5b are moved in the X-direction for scanning the surface of the PDP 2 with the sensors comprising arrayed photodetectors. FIG. 6B shows the image that is input from the TV camera 5r, which is equipped with the red band-pass filter 7r. The red fluorescent substance region 3r is indicated as the highest density level (white) region H, whereas the portions coated with green or blue fluorescent substance 3g and 3b appear as the lowest density level (black) regions L. Also, impurities and gaps in the fluorescent substance are represented as low density levels (black) $L_1$, that are different from L, and portions where the red fluorescent substance 3r has been coated onto the rib 2a or into the coating portions of the green and blue fluorescent substance 3g and 3b appear as intermediate density level (white) regions M. The data processing is carried out with the numerical values (0 to 255) indicating the density level.

The area in this image that is to be processed is designated as the processing area at step 2. Then, threshold values are set for each element of the photodetectors in the sensors for performing thresholding of the area. A series of connected pixels, or a run, is extracted from each line of scanning sensors at step 3. For example, taking the area including the band regions denoted at L in FIG. 6B as the processing area, an appropriate threshold value is set for this area, and the portions corresponding to M are extracted as runs or lines of connected pixels having a same threshold value. Or, the area including the band regions denoted at H is taken as the processing area, an appropriate threshold value is set, and the portions corresponding to $L_1$ are extracted as runs. As the data for these runs or series of connected pixels, the data representative of the start point $x_1$ and the end point $x_2$ of each run are obtained. Such data will be hereinafter referred to as run length data.

Subsequently, the extracted run length data is compressed into run length codes. When compressing the extracted data into the run length codes, noise is discriminated from the actual red fluorescent substance coating portions based on the length of the runs (run length data), and deficiency candidates are selected. That is, since the length of a portion where the red fluorescent substance is coated should be within a predetermined range, if there are any series of pixels of a length that is outside of this predetermined range, such are cut as noise. The above-mentioned run-length cutting unit 17 effects such processing. Thus, unnecessary data are cut, thereby making fast processing possible. During this process, the average density data of the runs are stored along with the run length data (step 4). Then, deficiency candidate regions are extracted from the run length code by performing a labeling process, i.e., by determining whether there are connected components based on a comparison with 8 neighbor pixels (step 5). A plurality of characteristic quantities are detected from the individual deficiency candidate regions (step 6), and the acceptability of the candidate regions is judged depending on these characteristic quantities (step 7). The positions of the detected deficiency regions are displayed individually on the display 22 at step 8. Preferably, the deficiency image is then picked up at high magnification with the review camera 23, and displayed on the display 22 for visual confirmation.

The examination whether the green and blue fluorescent substances 3g and 3b have been coated onto the ribs 2a or into other fluorescent coating regions is performed by the image processing unit 51 in parallel in a similar process on the image from the cameras 5g and 5b provided with green and blue band-pass filters 7g and 7b.

When the scanning in the X-direction is finished, the TV cameras 5r, 5g and 5b are moved a certain distance in the Y-direction to inspect the fluorescent substance by again scanning in the X-direction, and this process is repeated to inspect the coating with fluorescent substance on the entire PDP 2.

If the band regions H in FIG. 6B are not perpendicular to the arrayed photodetectors, and portions of the band regions H intersect with either the left or the right edge of the processing area, it is preferable that the unnecessary run length data of these intersecting portions be eliminated right away, thereby allowing for faster processing.

Further, after picking up an image by the photodetectors, it is preferable to convert only a portion of the image between two lines separated by a certain distance (for example 10 lines) into numerical image data, to be subjected to the above-described image processing. Thereby, the influence of color variations affecting the entire PDP can be purged, making examinations possible that reliably pick up on local changes.

According to the apparatus for inspecting a fluorescent substance of the present invention, as described above, even delicate color mixing can reliably be identified. Therefore, the present invention method and apparatus can favorably be applied for an inspection process in the manufacture of plasma display panels or cathode-ray tubes on which fluorescent substances are coated.

Although the present invention has been fully described in connection with the preferred embodiment thereof, it is to be noted that various changes and modifications apparent to those skilled in the art are to be understood as included within the scope of the present invention as defined by the appended claims unless they depart therefrom.

What is claimed is:

1. An apparatus for inspecting a coating of a fluorescent substance on a subject to be inspected, comprising:
    a table for supporting the subject to be inspected;
    an illumination device for irradiating UV light onto the fluorescent substance for causing the fluorescent substance to emit light;
    an imaging device for imaging an image of light emission of the fluorescent substance; and
    a plurality of filters provided between the imaging device and the subject, the plurality of filters allowing only light of specified wavelengths, in accordance with light emission characteristics of the fluorescent substance, pass toward the imaging device, wherein the plurality of filters include a first filter that passes only light of wavelengths 580 to 660 nm, a second filter that passes only light of wavelengths 500 to 580 nm, and a third filter that passes only light of wavelength 400 to 500 nm.

2. The apparatus according to claim 1, wherein the illumination device irradiates UV light of wavelengths in a range of from 220 to 240 nm.

3. The apparatus according to claim 1, wherein the subject of inspection is either one of a plasma display panel and a cathode-ray tube.

4. The apparatus according to claim 3, further comprising a visible rays cutting filter for preventing direct irradiation of visible light from the illumination device into the imaging device.

5. The apparatus according to claim 3, wherein the illumination device includes a light source, and a mirror for focusing by reflection the UV light emitted radially from the light source at a position at a specified distance from the light source.

6. The apparatus according to claim 3, further comprising a device for decreasing oxygen density of an atmosphere at the location where UV light is irradiated by the illumination device onto the fluorescent substance below the oxygen density in air.

7. The apparatus according to claim 3, further comprising:
    the imaging device including photodetectors arranged in a line
    the coating of the fluorescent substance being inspected continuously by effecting relative movement of the table and the imaging device in a direction that is perpendicular to a direction in which the photodetectors are arranged;
    a unit for individually thresholding signals that are input from each of the photodetectors; and
    a unit for checking for deficiency candidates based on run lengths detected by the thresholding.

8. The apparatus according to claim 7, wherein run lengths and average densities of runs are calculated as compressed data of deficiency candidate regions.

9. The apparatus according to claim 3, further comprising a display, a review camera, and a unit for displaying an image of deficiency portions imaged by the review camera on the display for automatic review of examination results.

10. A method for inspecting a coating of a fluorescent substance on a subject of inspection, comprising the procedures of:
    providing the subject on a table;
    irradiating UV light onto the fluorescent substance causing the fluorescent substance to emit light with an illumination device;
    imaging an image of light emitted from the fluorescent substance with an imaging device; and
    passing the light emitted from the fluorescent substance through a plurality of filters that pass only light of specified wavelengths in accordance with light emission characteristics of the fluorescent substance before the flourescent substance is imaged by the imaging device, wherein the plurality of filters include a first filter that passes only light of wavelengths 580 to 660 nm, a second filter that passes only light of wavelengths 500 to 580 nm, and a third filter that passes only light of wavelength 400 to 500 nm.

11. The method according to claim 10, wherein the subject of inspection is either one of a plasma display panel and a cathode-ray tube.

12. The method according to claim 10, wherein the UV light irradiated onto the fluorescent substance is of wavelengths in a range of from 220 to 240 nm.

13. A manufacturing method of plasma display panels including an inspection process in accordance with the method as set forth in claim 10.

14. A manufacturing method of cathode-ray tubes including an inspection process in accordance with the method as set forth in claim 10.

15. The method according to claim 10, further comprising the step of providing a visible rays cutting filter for preventing direct irradiation of visible light from the irradiation device into the imaging device.

16. The method according to claim 10, wherein the irradiation device includes a light source, and a mirror for focusing by reflection the UV light emitted radially from the light source at a position at a specified distance from the light source.

17. The method according to claim 10, further comprising the step of providing a device for decreasing oxygen density of an atmosphere at the location where UV light is irradiated by the illumination device onto the fluorescent substance below the oxygen density in air.

18. The method according to claim 10, further comprising the steps of:

providing photodetectors arranged in a straight line in the imaging device;

continuously inspecting the coating of the fluorescent substance by effecting relative movement of the imaging device and the table;

providing a unit for individually thresholding signals that are input from each of the photodetectors; and providing a unit for checking for deficiency candidates based on run lengths detected by the thresholding.

19. The method according to claim 18, wherein run lengths and average densities are calculated as compressed data of deficiency candidate regions.

20. The method according to claim 10, wherein the table is a positioning table for positioning the subject to be inspected.

21. The method according to claim 10, further comprising the step of providing a review camera and a unit for displaying an image of deficiency portions imaged by the review camera on the display for automatic review of examination results.

* * * * *